United States Patent [19]

Kubitza et al.

[11] 4,292,350

[45] Sep. 29, 1981

[54] ISOCYANATE MIXTURE AND ITS USE AS BINDER IN ONE-COMPONENT LACQUERS

[75] Inventors: Werner Kubitza; Gerhard Mennicken, both of Leverkusen; Josef Pedain, Cologne, all of Fed. Rep. of Germany

[73] Assignee: Bayer Aktiengesellschaft, Leverkusen, Fed. Rep. of Germany

[21] Appl. No.: 84,021

[22] Filed: Oct. 12, 1979

[30] Foreign Application Priority Data

Oct. 19, 1978 [DE] Fed. Rep. of Germany ....... 2845514

[51] Int. Cl.³ .............................................. C08L 75/04
[52] U.S. Cl. .................................... 427/385.5; 528/67; 260/31.2 N; 260/32.8 N; 260/33.6 R; 427/385.5
[58] Field of Search .................. 260/31.2 N; 525/127; 528/67

[56] References Cited

U.S. PATENT DOCUMENTS

| | | | |
|---|---|---|---|
| 3,205,201 | 9/1965 | Friedrich et al. | 260/31.2 |
| 3,487,080 | 12/1969 | Matsui et al. | 544/193 |
| 3,619,338 | 11/1971 | Gillman et al. | 428/286 |
| 3,992,316 | 11/1976 | Pedain et al. | 260/31.2 |
| 4,211,804 | 7/1980 | Brizzolara | 427/385.5 |

FOREIGN PATENT DOCUMENTS

| | | | |
|---|---|---|---|
| 1029890 | 4/1978 | Canada | 402/131 |
| 1050257 | 12/1966 | United Kingdom | 260/31.2 |
| 1305922 | 2/1973 | United Kingdom | 260/31.2 |
| 1458564 | 12/1976 | United Kingdom | 260/31.2 |

*Primary Examiner*—Joseph L. Schofer
*Assistant Examiner*—Peter F. Kulkosky
*Attorney, Agent, or Firm*—Gene Harsh; Lawrence S. Pope; Thomas W. Roy

[57] ABSTRACT

Isocyanate mixtures which are stable in the absence of moisture, and are curable by atmospheric moisture and which have low viscosities are obtained by mixing polyisocyanates containing biuret, allophanate or urethane bonds and functionalities in excess of 2 with monoisocyanates. These mixtures are used to coat substrates and the exposure of the coated substrates to atmospheric moisture results in cured coatings.

7 Claims, No Drawings

ISOCYANATE MIXTURE AND ITS USE AS BINDER IN ONE-COMPONENT LACQUERS

FIELD OF THE INVENTION

This invention relates to new, physiologically harmless isocyanate mixtures suitable for use as binders in solvent-free one-component lacquers, and to their use.

BACKGROUND OF THE INVENTION

Low solvent and solvent-free two-component polyurethane lacquers are known (see e.g. German Auslegeschrift No. 2,006,055, German Auslegeschrift No. 2,304,893 or Canadian Pat. No. 1,029,890). One major disadvantage of these two-component systems is their limited pot life.

One-component binders based on organic isocyanates which have a virtually unlimited storage life in the absence of moisture and can be used for the preparation of solvent-free or low solvent lacquers which can be applied by any of the conventional methods of lacquer technology and are hardened by atmospheric moisture have not hitherto been known. The known one-component systems based on isocyanates, i.e. the known prepolymers containing isocyanate groups, generally have too high a viscosity for application by, for example, spraying without the use of a solvent.

It was an object of the present invention to provide such one-component binders. It could be solved by means of the isocyanate mixtures described in detail below.

SUMMARY OF THE INVENTION

This invention relates to an isocyanate mixture suitable for use as a binder for one-component lacquers, which mixture can be stored in the absence of moisture is cross-linked by moisture with the formation of urea groups, has a viscosity of from about 30 to 200 seconds measured in a DIN cup 4 according to DIN 53 211, and contains a maximum of about 0.7% by weight of readily volatile organic diisocyanates, characterized in that it comprises a mixture of:

(a) at least one lacquer polyisocyanate which contains biuret, urethane and/or isocyanurate groups and has an average isocyanate functionality greater than 2 and an isocyanate content of from about 13 to 30% by weight, and (b) at least one monoisocyanate corresponding to the following general formula:

$R_1$—O—CO—NH—$R_2$—NCO wherein
$R_1$ represents a hydrocarbon group having from 1 to 18 carbon atoms optionally interrupted by ether bridges and
$R_2$ represents a group such as is obtained by removal of the isocyanate groups from an aliphatic, cycloaliphatic, araliphatic or aromatic diisocyanate having a molecular weight of from about 140 to 300,
in which the proportion by weight of components (a):(b) is equal to, or greater than, about 1:1, and the average isocyanate functionality of the mixture is greater than about 1.8.

This invention also relates to the use of these isocyanate mixtures as binders in one-component lacquers which can be hardened by moisture.

DETAILED DESCRIPTION OF THE INVENTION

Component (a) of the mixtures according to the present invention consists of lacquer polyisocyanates, i.e. in particular polyisocyanates having an average isocyanate functionality greater than 2, preferably from about 2.5 to 6, which contain biuret, urethane or isocyanurate groups. These polyisocyanates preferably have aromatically, cycloaliphatically or aliphatically bound isocyanate groups. For light-fast coatings, polyisocyanates which have aliphatically and/or cycloaliphatically bound isocyanate groups are preferred. The lacquer polyisocyanates to be used according to the present invention are prepared by a known method of modification of simple organic diisocyanates with the formation of biuret, urethane or isocyanurate groups, in which any excess of unmodified monomeric starting isocyanates left after the modification reaction is removed by a known method, preferably by distillation, so that the lacquer polyisocyanates used according to the present invention contain at the most about 0.7% by weight, preferably about 0.5% by weight of excess diisocyanate. The lacquer polyisocyanates to be used according to the present invention generally have an isocyanate content, based on the solid substances, of from about 10 to 30% by weight and they preferably have a maximum viscosity of about 4000 mPa.s/20° C.

Suitable diisocyanates for the preparation of the lacquer polyisocyanates include, for example, 2,4- and/or 2,6-diisocyanatotoluene, 2,4'-diisocyanato-dicyclohexylmethane, 4,4'-diisocyanato-dicyclohexylmethane, hexamethylene diisocyanate and 1-isocyanato-3,3,5-trimethyl-5-isocyanatomethyl-cyclohexane (IPDI). 2,4-Diisocyanato-toluene, hexamethylene diisocyanate and IPDI are the preferred diisocyanates for the preparation of the lacquer polyisocyanates used according to the present invention. Preparation of the lacquer polyisocyanates from the starting diisocyanates exemplified above is carried out by methods known in the art. Thus, for example, lacquer polyisocyanates containing biuret groups may be prepared by the process according to U.S. Pat. Nos. 3,124,605, 3,358,010, 3,903,126, 3,903,127 or 2,976,622 all incorporated herein by reference. The preparation of urethane polyisocyanates used according to the present invention may be carried out, for example, according to U.S. Pat. No. 3,183,112 incorporated herein by reference and the preparation of lacquer polyisocyanates with isocyanurate groups which are suitable for the purpose of the present invention may be carried out, for example, by the processes according to British Pat. Nos. 1,060,430, 1,234,972, 1,506,373 or 1,458,654 or according to U.S. Pat. Nos. 3,394,111, 3,645,979 or 3,919,218 all incorporated herein by reference or according to German Patent Application P 2 839 133.5.

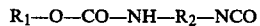

Particularly preferred lacquer polyisocyanates include the polyisocyanates having biuret group according to U.S. Pat. No. 3,124,605 and particularly U.S. Pat. No. 3,903,127, especially those based on hexamethylene diisocyanate; polyisocyanates having urethane groups according to U.S. Pat. No. 3,183,112, especially those based on 2,4-diisocyanatotoluene, trimethylolpropane and the various butanediols, and polyisocyanates having isocyanurate groups according to the above-mentioned patents, in particular the corresponding isocyanurate polyisocyanates based on 2,4-diisocyanatotoluene and its mixtures with hexamethylene diisocyanate or those based on IPDI.

Component (b) of the mixture according to the present invention consists of monoisocyanates corresponding to the following general formula:

$$R_1-O-CO-NH-R_2-NCO$$

wherein $R_1$ and $R_2$ are defined as above.

$R_1$ preferably represents a saturated aliphatic hydrocarbon group having from 6 to 12 carbon atoms optionally interrupted by ether oxygen atoms, in particular a saturated aliphatic hydrocarbon group having from 6 to 12 carbon atoms and a branched carbon chain, and $R_2$ preferably represents a saturated aliphatic hydrocarbon group having from 4 to 12, in particular 6 carbon atoms or a saturated cycloaliphatic hydrocarbon group having from 6 to 15 carbon atoms, at least 2 carbon atoms being in each case situated between the two nitrogen atoms in the above formula.

These monoisocyanates can be prepared by a simple process of reacting excess quantities of a diisocyanate $R_2(NCO)_2$ with a hydroxyl compound $R_1-OH$ followed by removal of unreacted excess diisocyanate by distillation, for example in a thin layer evaporator.

The following are examples of suitable diisocyanates $R_2(NCO)_2$: tetramethylene diisocyanate, hexamethylene diisocyanate, dodecamethylene diisocyanate, 1,3- and 1,4-diisocyanatocyclohexane, 2,4- and 2,6-diisocyanatotoluene, 1-methyl-2,4-diisocyanatocyclohexane, 4,4'-diisocyanatodicyclohexylmethane or 1-isocyanato-3,3,5-trimethyl-5-isocyanatomethyl-cyclohexane (IPDI).

The diisocyanate preferably used is hexamethylenediisocyanate.

The following are examples of suitable hydroxyl compounds $R_1-OH$: methanol, ethanol, i-propanol, i-butanol, n-dodecanol, n-octadecanol, ethoxyethanol, ethoxy-ethoxyethanol, propoxyethanol, and cyclohexanol; branched chain alcohols such as neopentyl alcohol, 2-ethylhexanol or the isomeric trimethylhexanols being particularly preferred.

The diisocyanates and alcohols used for the preparation of the monoisocyanates are otherwise chosen so that the reaction products corresponding to the above formula are low viscosity monoisocyanates which are liquid at room temperature.

Before the mixtures according to the present invention are prepared, both component (a) and component (b) are preferably freed from any physiologically harmful, volatile diisocyanates used for their preparation, for example by evaporation in a thin layer evaporator, so that the mixtures according to the invention contain less than about 0.7% by weight, preferably less than about 0.5% by weight of such diisocyanates.

Preparation of the mixtures according to the present invention is carried out by simply mixing components (a) and (b) in proportions by weight of (a) to (b) equal to, or greater than, about 1:1, preferably in the range of from about 2:1 to 5:1. The proportions of components (a) and (b) are otherwise calculated so that the mixtures have an average isocyanate functionality greater than about 1.8, preferably from about 2 to 3, and a viscosity measured according to DIN 53 211 in a DIN cup 4 of from about 30 to 200 seconds, preferably from about 60 to 170 seconds.

The mixtures according to the present invention are low viscosity binders which have a virtually unlimited storage life in the absence of moisture and undergo cross-linking in the presence of moisture, in particular atmospheric moisture, with the formation of urea groups. Owing to their low viscosity, they are suitable for the preparation of solvent-free or low solvent one-component lacquers. The lacquers can therefore be prepared without the use of solvents. In some cases, a small quantity of lacquer solvents or plasticizers, i.e. from about 0 to 15% by weight, based on the binder, is sufficient to adjust the coating compound to the desired initial viscosity. Suitable lacquer solvents of this type include, for example, ethyl acetate, butyl acetate, methyl ethyl ketone, methyl isobutyl ketone and xylene. Examples of suitable plasticizers include dibutyl phthalate, tributylphosphate and methyl adipate.

For their use according to the present invention, the mixtures according to the invention may be mixed with any of the conventional auxiliaries and additives used in lacquer technology, e.g. catalysts for the isocyanate-water reaction, pigments, fillers, levelling agents and drying agents. Lacquers ready for use generally have an outflow viscosity of from about 20 to 400 seconds, preferably from about 50 to 200 seconds, measured in a DIN cup 4 according to DIN 53 211. They are physiologically harmless owing to the absence of readily volatile diisocyanates, and they can be applied to their substrates by conventional methods, such as spread coating, spraying or application with rollers. They are suitable inter alia for the coating of metals, wood, plastics, concrete, paper or asbestos cement. Since they are preferably processed solvent-free, no ecological problems or problems due to unpleasant odors occur either during or after their application. The lacquers may be used inter alia for protective and decorative coatings, e.g. in the foodstuff industry, without any risk of affecting the flavor of the food.

The isocyanates described below are used in the examples which follow.

Monoisocyanate A

Reaction product of 1 mol of 2-ethylhexanol and 3 mol of a mixture of 80 parts of 2,4- and 20 parts of 2,6-diisocyanatotoluene with the subsequent removal of excess diisocyanate. The low viscosity monoisocyanate has an isocyanate content of 14.0% by weight and a monomeric diisocyanate content of 0.3% by weight.

Monoisocyanate B

Reaction product of 1 mol of 2-ethylhexanol and 3 mol of hexamethylene diisocyanate with the subsequent removal of excess diisocyanate by distillation. The low viscosity monoisocyanate has an isocyanate content of 14.1% by weight and a monomeric hexamethylene diisocyanate content of 0.2% by weight.

Polyisocyanate C

Biuret polyisocyanate mixture consisting substantially of tris-(isocyanatohexyl)-biuret and prepared by the biuretization of hexamethylene diisocyanate according to U.S. Pat. No. 3,903,127. Isocyanate content: 23.5% by weight; free hexamethylene diisocyanate content: <0.7% by weight; average isocyanate functionality: >3; viscosity (DIN cup 4 according to DIN 53 211): 270 seconds (2400 mPa.s/20° C.

Polyisocyanate D 1.2 g of tri-n-butylphosphine are added to 336 g of hexamethylene diisocyanate and the mixture is stirred for about 8 hours at 50°-60° C. By the end of this time, the isocyanate content has fallen from 49.5% to 35–36%. The reaction is stopped by the addition of 1.5 g of benzoyl chloride and brief heating to 80° C. and the thin liquid reaction product obtained is distilled twice over in a thin layer evaporator (vacuum: 0.3 torr, temperature of circulating heating medium: 160° to 170° C.). 161 g of distillate and 170 g of oligomer having an isocyanate content of 21.1% and a free hexamethylene diisocyanate content of less than 0.7% are obtained. The viscosity is 1000 mPa.s/20° C.

EXAMPLES

Example 1

25 parts by weight of monoisocyanate A, 25 parts by weight of monoisocyanate B and 100 parts by weight of monoisocyanate C are mixed together. The mixture has a viscosity of 165 seconds measured in a DIN cup 4 according to DIN 53 211, an average isocyanate functionality above 1.8 and an isocyanate content of 20.3% by weight. After the addition of 0.75 parts by weight of dibutyl tin dilaurate as a catalyst, a clear lacquer is obtained which has a virtually unlimited storage life in the absence of moisture and which can be applied by roller to form a lacquer film which dries overnight with atmospheric moisture. The lacquer film has a hardness according to DIN 53 157 of about 65 seconds and an Erichsen cupping according to DIN 53 156 of 9 mm.

The addition of 15 parts by weight of adipic acid dimethyl ester to the above-mentioned mixture results in a clear lacquer having a viscosity according to DIN 53 211 of 70 seconds, which can be applied by the "airless" spraying process.

Example 2

100 Parts by weight of polyisocyanate C are mixed with 50 parts by weight of monoisocyanate B. The mixture has a viscosity of 110 seconds measured in a DIN cup 4 according to DIN 53 211, an average isocyanate functionality of >1.8 and an isocyanate content of 20.4% by weight. The addition of 0.75 parts by weight of dibutyl tin dilaurate as a catalyst results in a clear lacquer which remains in a suitable state for application for an unlimited length of time in the absence of moisture and which hardens overnight at room temperature to form a tough elastic film. The hardened film has a pendulum hardness according to DIN 53 157 of about 60 seconds and an Erichsen cupping according to DIN 53 156 of 10 mm.

The clear lacquer obtained without the addition of monoisocyanate B could not be applied with either a brush or roller due to its high viscosity.

Example 3

100 Parts by weight of polyisocyanate C are mixed with 50 parts by weight of monoisocyanate B. The mixture has a viscosity measured in a DIN cup 4 according to DIN 53 211 of 110 seconds, an isocyanate content of 20.4% by weight and an average isocyanate functionality of >1.8. The addition of 45 parts by weight of titanium dioxide (rutile), 5.4 parts by weight of tosylisocyanate (drier for the pigment) and 0.75 parts by weight of dibutyl tin dilaurate results in a solvent-free, moisture hardening one-component coating compound having a viscosity of 170 seconds according to DIN 53 211 which can be applied with a brush or roller. The lacquer remains in a suitable state for application for an unlimited length of time and dries at room temperature to form a tough elastic film. The film has a pendulum hardness according to DIN 53 157 of 55 seconds and an Erichsen cupping according to DIN 53 156 of 10 mm.

The coating compound obtained after the addition of 10 parts by weight of dimethyladipate has a viscosity according to DIN 53 211 of about 95 seconds.

Without the addition of monoisocyanate B, the pigmented mixture would have a viscosity of over 5 minutes (DIN 53 211) even if the pigment content were reduced to 30 parts by weight, and it could not be applied with either a brush or roller.

Example 4

100 Parts by weight each of monoisocyanate B, polyisocyanate C and polyisocyanate D are mixed together. The mixture has a viscosity according to DIN 53 211 of 60 seconds, an average isocyanate functionality of >1.8 and an isocyanate content of 19.7% by weight. The addition of 150 parts by weight of titanium dioxide (rutile), 18 parts by weight of tosylisocyanate and 1.5 parts by weight of dibutyl tin dilaurate results in a solvent-free, moisture hardening one-component coating compound which has an outflow viscosity of about 110 seconds according to DIN 53 211 and which can be applied with a brush or roller. The coating compound obtained after the addition of 30 parts by weight of adipic acid dimethyl ester has a viscosity measured according to DIN 53 211 of about 55 seconds. This coating compound can be applied by various methods, including airless spraying.

Without the addition of monoisocyanate and plasticizer, the mixture obtained would have an outflow viscosity of over 300 seconds even if the pigment content were reduced to 100 parts by weight, and it could not be applied either by brush coating or with a roller.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. An isocyanate mixture suitable for use as a binder for one-component lacquers, which mixture is stable in storage in the absence of moisture and is cross-linked by moisture with the formation of urea groups and has a solvent-free viscosity measured in a DIN cup 4 according to DIN 53 211 of from about 30 to 200 seconds and contains a maximum of about 0.7% by weight of readily volatile organic diisocyanates, comprising a mixture of:
    (a) at least one lacquer polyisocyanate containing biuret, urethane and/or isocyanurate groups and having an average isocyanate functionality greater than 2 and an isocyanate content of from about 13 to 30% by weight and
    (b) at least one monoisocyanate corresponding to the following general formula:

$$R_1-O-CO-NH-R_2-NCO$$

wherein
    $R_1$ represents a hydrocarbon group having from 1 to 18 carbon atoms optionally interrupted by ether bridges and
    $R_2$ represents a group such as is obtained by removal of the isocyanate groups from an aliphatic, cycloaliphatic, araliphatic or aromatic diisocyanate having a molecular weight of from about 140 to 300, the proportion by weight of component (a) to component (b) being from about 2:1 to 5:1, and the average isocyanate functionality of the mixture being greater than about 1.8.

2. A process of coating a substrate comprising
(1) applying a lacquer composition containing as a binder an isocyanate mixture having an isocyanate functionality greater than 1.8, a solvent-free viscosity of between about 30 and 200 seconds in a DIN cup 4 according to DIN 53 211 and a volatile diisocyanate content of less than about 0.7 wt % to said substrate, said mixture comprised of
(a) an organic polyisocyanate having an average isocyanate functionality greater than 2, containing urethane, biuret and/or isocyanurate groups and having an isocyanate content of between about 13 and 30 wt %, and
(b) a monoisocyanate of the general formula:

$R_1$—O—CO—NH—$R_2$—NCO wherein
$R_1$ represents a hydrocarbon group having 1 to 18 carbon atoms and optionally interrupted by ether bridges, and
$R_2$ represents the isocyanate free residue of an aliphatic, cycloaliphatic, araliphatic or aromatic diisocyanate having a molecular weight of between about 140 and 300,
said components mixed in a ratio of a:b of from about 2:1 to 5:1,
(2) exposing said substrate to atmospheric moisture for a sufficient time to cause the isocyanate groups of said mixture to react with the moisture and form a cured coating.

3. The isocyanate mixture of claim 1 wherein the polyisocyanate is an adduct of hexamethylene diisocyanate.

4. The isocyanate mixture of claim 1 wherein the monoisocyanate is an adduct of hexamethylene diisocyanate or toluene diisocyanate.

5. In a process for the preparation of one-component lacquers which can be hardened by the action of moisture, the improvement comprising using the isocyanate mixture of claim 1 as a binder.

6. An isocyanate mixture suitable for use as a binder for one-component lacquers, which mixture is stable in storage in the absence of moisture and is cross-linked by moisture with the formation of urea groups and has a solvent-free viscosity measured in a DIN cup 4 according to DIN 53 211 of from about 30 to 200 seconds and contains a maximum of about 0.7% by weight of readily volatile organic diisocyanates, consisting essentially of a mixture of:
(a) at least one lacquer polyisocyanate containing biuret, urethane and/or isocyanurate groups and having an average isocyanate functionality greater than 2 and an isocyanate content of from about 13 to 30% by weight and
(b) at least one monoisocyanate corresponding to the following general formula:

$R_1$—O—CO—NH—$R_2$—NCO wherein
$R_1$ represents a hydrocarbon group having from 1 to 18 carbon atoms optionally interrupted by ether bridges and
$R_2$ represents a group such as is obtained by removal of the isocyanate groups from an aliphatic, cycloaliphatic, araliphatic or aromatic diisocyanate having a molecular weight of from about 140 to 300, the proportion by weight of component (a) to component (b) being from about 2:1 to 5:1 and the average isocyanate functionality of the mixture being greater than about 1.8.

7. A process of coating a substrate comprising
(1) applying a lacquer composition containing as a binder an isocyanate mixture having an isocyanate functionality greater than 1.8, a solvent-free viscosity of between about 30 and 200 seconds in a DIN cup 4 according to DIN 53 211 and a volatile diisocyanate content of less than about 0.7 wt.% to said substrate, said mixture consisting essentially of
(a) an organic polyisocyanate having an average isocyanate functionality greater than 2, containing urethane, biuret and/or isocyanurate groups having an isocyanate content of between about 13 and 30 wt.%, and
(b) a monoisocyanate of the general formula $R_1$—O—CO—NH—$R_2$—NCO wherein
$R_1$ represents a hydrocarbon group having 1 to 18 carbon atoms and optionally interrupted by ether bridges, and
$R_2$ represents the isocyanate free residue of an aliphatic, cycloaliphatic, araliphatic or aromatic diisocyanate having a molecular weight of between about 140 and 300,
said components mixed in a ratio of a:b of from about 2:1 to 5:1,
(2) exposing said substrate to atmospheric moisture for a sufficient time to cause the isocyanate groups of said mixture to react with the moisture and form a cured coating.

* * * * *